(12) United States Patent
Davies et al.

(10) Patent No.: US 9,631,230 B2
(45) Date of Patent: Apr. 25, 2017

(54) METHODS AND DEVICES FOR DIGITAL PCR

(75) Inventors: Mark Davies, Limerick (IE); Tara Dalton, Patrickswell (IE)

(73) Assignee: STOKES BIO LTD, Limerick (IE)

(*) Notice: Subject to any disclaimer, the term of this patent is extended or adjusted under 35 U.S.C. 154(b) by 925 days.

(21) Appl. No.: 12/539,343

(22) Filed: Aug. 11, 2009

(65) Prior Publication Data

US 2010/0092973 A1    Apr. 15, 2010

Related U.S. Application Data

(60) Provisional application No. 61/088,142, filed on Aug. 12, 2008.

(51) Int. Cl.
*C12Q 1/68* (2006.01)
*B01L 3/00* (2006.01)
*B01L 7/00* (2006.01)

(52) U.S. Cl.
CPC ...... *C12Q 1/6851* (2013.01); *B01L 3/502784* (2013.01); *B01L 7/525* (2013.01); *B01L 2300/0838* (2013.01); *B01L 2300/0867* (2013.01); *B01L 2400/0487* (2013.01)

(58) Field of Classification Search
None
See application file for complete search history.

(56) References Cited

U.S. PATENT DOCUMENTS

| | | | |
|---|---|---|---|
| 7,579,172 B2 * | 8/2009 | Cho et al. | 435/91.2 |
| 7,630,837 B2 * | 12/2009 | Eyre et al. | 702/19 |
| 7,888,017 B2 * | 2/2011 | Quake et al. | 435/6.12 |
| 2001/0041357 A1 | 11/2001 | Fouillet et al. | |
| 2004/0224325 A1* | 11/2004 | Knapp et al. | 435/6 |
| 2005/0202489 A1 | 9/2005 | Cho et al. | |

FOREIGN PATENT DOCUMENTS

| | | |
|---|---|---|
| WO | 2005/002730 | 1/2005 |
| WO | 2006/089192 | 8/2006 |
| WO | 2007/091228 | 8/2007 |
| WO | 2007/091230 | 8/2007 |
| WO | 2008/038259 | 4/2008 |
| WO | 2010/018465 A3 | 2/2010 |

OTHER PUBLICATIONS

Heid et al. Genome Research 6:986-994 (1996).*
Beer, N.R. et al., "On-chip single-copy real-time reverse-transcription PCR in On-chip single-copy real-time reverse-transcription PCR in isolated picoliter droplets", *Analytical Chemistry*, vol. 80, No. 6, Mar. 15, 2008, 1854-1858.
Beer, N.R. et al., "On-chip, real-time, single-copy polymerase chain reaction in picoliter droplets", *Analytical Chemistry*, vol. 79, No. 2, Nov. 15, 2007, 8471-8475.
Kiss, M.M. et al., "High-throughput quantitative polymerase chain reaction in picoliter droplets", *Analytical Chemistry*, vol. 80, No. 23, Dec. 1, 2008, 8975-8981.
International Application No. PCT/IB2009/007568, International Search Report dated Apr. 15, 2010.
International Application No. PCT/IB2009/007568, International Preliminary Report on Patentability mailed Feb. 24, 2011.

* cited by examiner

*Primary Examiner* — Samuel Woolwine
(74) *Attorney, Agent, or Firm* — Jones Robb, PLLC

(57) ABSTRACT

The invention provides methods of conducting a nucleic acid reaction, including methods for performing digital PCR using a "droplet-in-oil" technology. In the methods, the starting sampled is segmented at least partially into a set of sample droplets each containing on average about one or fewer copies of a target nucleic acid. The droplets are passed in a continuous flow of immiscible carrier fluid through a channel that passes through a thermal cycler, whereby the target is amplified. In one implementation, the droplets are about 350 nl each and the number of positively amplified droplets is counted at the near-saturation point.

25 Claims, 7 Drawing Sheets

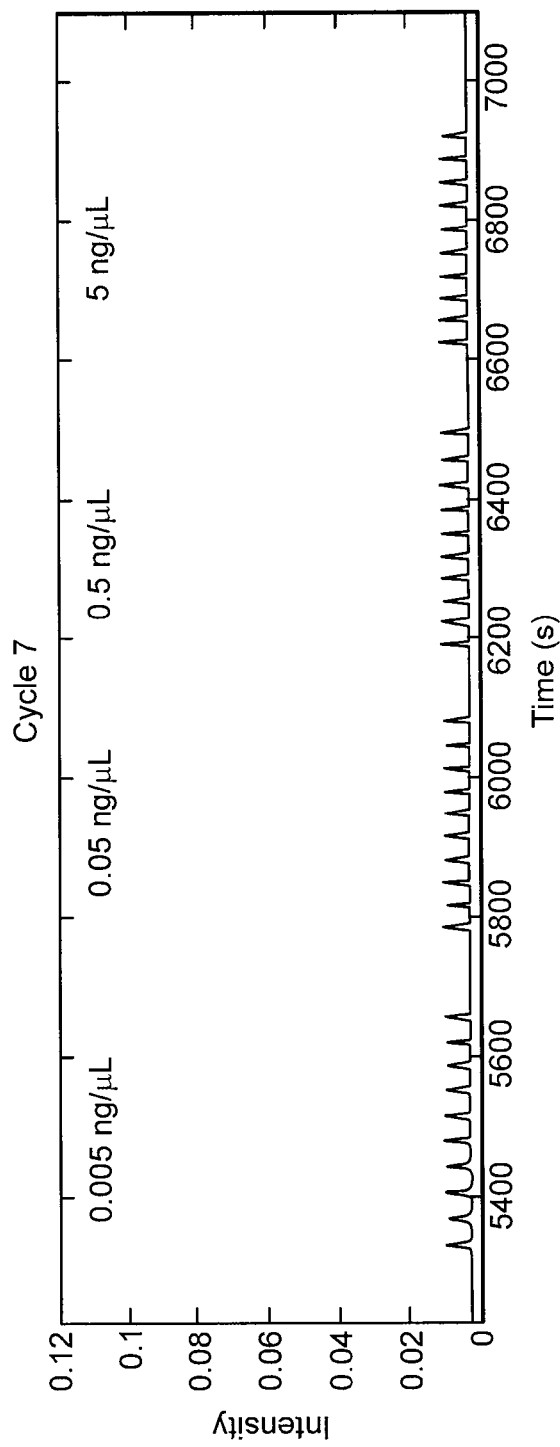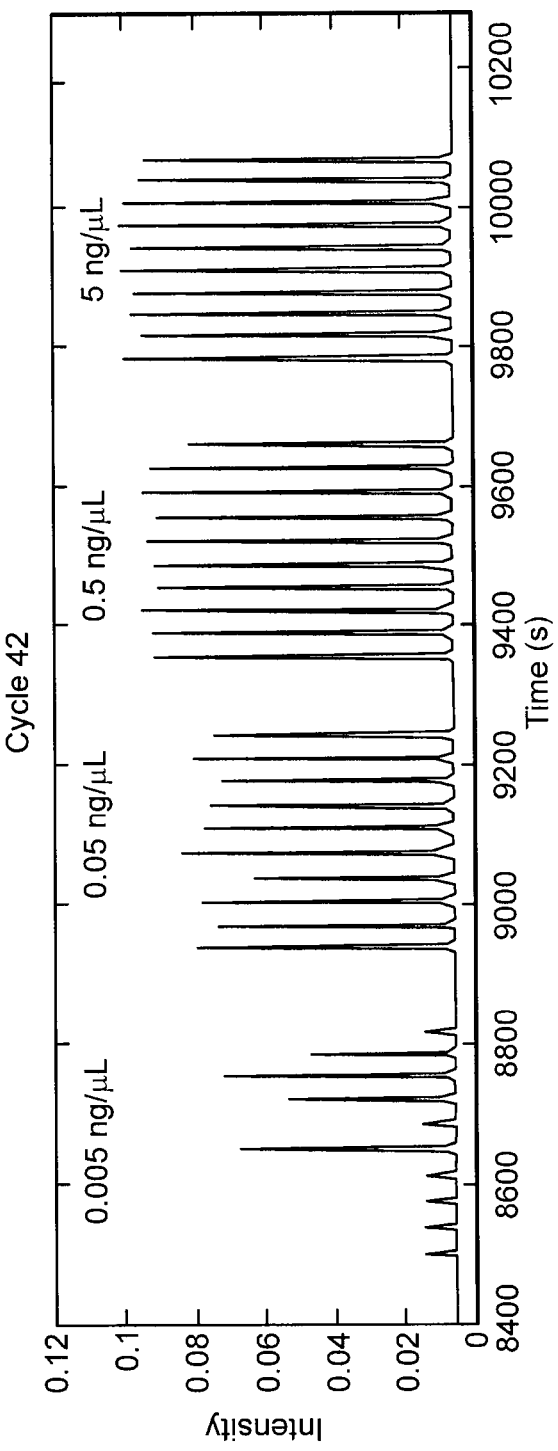

METHODS AND DEVICES FOR DIGITAL PCR

RELATED APPLICATIONS

The present application claims priority to U.S. Provisional Application No. 61/088,142, filed Aug. 12, 2008, the contents of which are incorporated by reference.

TECHNICAL FIELD

The invention relates to methods and devices for conducting nucleic acid amplification reactions, including the polymerase chain reaction (PCR).

BACKGROUND

PCR is a molecular amplification method routinely practiced in medical and bioresearch settings for a variety of tasks, such as the detection of hereditary diseases, the identification of genetic fingerprints, the diagnosis of infectious diseases, the cloning of genes, paternity testing, and other types of nucleic acid analysis. For a review of the PCR methodology, see, e.g., PCR Protocols (Methods in Molecular Biology) by Barlett and Stirling (eds.), Humana Press (2003); and PCR by McPherson and Moller, Taylor & Francis (2006).

Digital PCR is a technique that allows amplification of a single DNA template from a minimally diluted sample, thus, generating amplicons that are exclusively derived from one template and can be detected with different fluorophores or sequencing to discriminate different alleles (e.g., wild type vs. mutant or paternal vs. maternal alleles). For a review of the digital PCR methodology, see, e.g., Pohl et al., Expert Rev. Mol. Diagn., 4(1):41-7 (2004). The basic premise of the technique is to divide a large sample into a number of smaller subvolumes (segmented volumes), whereby the subvolumes contain on average a single copy of a target. Then, by counting the number of positives in the subvolumes, one may deduce the starting copy number of the target in the starting volume. Most commonly, multiple serial dilutions of a starting sample are used to arrive at the proper concentration in the subvolumes, the volumes of which are typically determined by a given PCR apparatus. This additional step increases the number of samples to be processed. A set of subvolumes may be tested that statistically represents the entire sample to reduce that number. However, under certain conditions, it may be necessary to detect very lowly expressed genes, resulting in a large number of blank segmented volumes and, thus, a large number of subvolumes to be evaluated. While making a sample more concentrated is a possibility in this case, doing so may introduce significant variability and losses (see, e.g., N. Blow, Nature Methods, 4:869-875 (2007). In addition, a more concentrated sample means that more sample is necessary to begin with.

Further considerations suggest that decreasing the volume of the amplification reaction might improve sensitivity for detecting a single molecule. For example, the TaqMan® assay requires near-saturating amounts of PCR amplification product to detect fluorescence. PCR reactions normally saturate at about $10^{11}$ product molecules/microliter due, in part, to reannealing of product strands. To reach this concentration of product after 30 cycles in a 10 µl PCR requires at least $10^3$ starting template molecules. If the volume of the PCR were reduced to ~10 nanoliters, then a single molecule could generate the required product to be detected by the TaqMan® assay. Attempts have been made to miniaturize PCR volumes (for a review, see, e.g., Zhang et al., Nucl. Acids Res., 35(13):4223-4237 (2007)). Nevertheless, as sample volumes decrease, amplification becomes increasingly more prone to biochemical surface absorption problems due to the increasing surface-to-volume ratio, as well as potential other sources of variability.

Therefore, there exists a need for methods and devices for accurately detecting or quantifying target copy numbers, including by means of the digital PCR.

SUMMARY OF THE INVENTION

The invention provides methods of conducting a nucleic acid reaction, including methods for performing digital PCR using "droplet-in-oil" technology, wherein a sample is segmented into droplets placed to a continuous flow of carrier fluid through a microfluidic channel. One example of such technology is described in PCT Pat. Appln. Pubs. WO 2007/091228 (corresponding U.S. Ser. No. 12/092,261), WO 2007/091230 (U.S. Ser. No. 12/093,132); and WO 2008/038259, and in the Examples. In some of these systems, termed "continuous flow PCR," the droplets are fully wrapped in the carrier fluid throughout the reaction and detection. The invention is based, at least in part, on the realization that sample droplets of 10-500 nl provide advantages for a PCR analysis of lowly expressed targets. Various aspects of the invention are described below.

In certain embodiments, the methods include:
 a) providing a starting sample comprising a target nucleic acid to be detected;
 b) segmenting at least part of the sample to provide a set of sample droplets in a continuous flow of immiscible carrier fluid (e.g., oil) through a channel (e.g., a capillary), each of said droplets containing on average about one or fewer copies of a target nucleic acid and reagents sufficient to perform a polymerase chain reaction;
 c) passing the droplets through a plurality of thermal zones thereby allowing the target nucleic acid, if present, to be amplified in each droplet; and
 d) detecting the presence or absence of, and/or determining the amount of, the amplified target nucleic acid in the droplets while in the flow.

The sample droplets have volumes of 0.1 pl-500 nl, preferably, 10-500 nl, more preferably, 30-350 nl, while the starting sample volumes are 0.05-5000 µl, preferably, 5-3500 µl. These volumes may include volumes of reagents (e.g., primer solution) added prior to the detection step. In certain embodiments, the droplets are spherical. In some embodiments, the droplets created by segmenting the starting sample are merged with a second set of droplets comprising one or more primers for the target nucleic acid, thereby producing the final droplets for the amplification reaction.

In some embodiments ("real-time detection"), the step of detecting or determining the amount is performed at multiple thermal cycles, thereby monitoring the amount of amplified target nucleic acid throughout the cycles, for example, in performing qPCR or real time PCR. Typically, the thermocycling is performed for at least a number of cycles required to reach the near-saturation level of the amplification. The number of cycles depends on the concentration of the target and other conditions and is typically between 20 and 40.

In preferred embodiments ("end-point detection"), the step of detecting or determining the amount is performed after the near-saturation point is reached. For the end-point detection, the starting copy number of the target nucleic acid may be determined by counting the number of positively amplified droplets in a given set of droplets.

The number of droplets in a set being analyzed is such that their combined volume is representative of the starting sample. The set of droplets contain the entire starting sample or only its part, depending on the number of copies of the target nucleic acid present or suspected to be present in the starting sample. The starting concentration of a target nucleic acid may be adjusted by diluting or by concentrating the starting sample. In illustrative embodiments, the set of droplets contains a train of 10 droplets, and 0.005 ng/µl cDNA in the starting sample.

The invention further provides methods of processing a plurality of starting samples in parallel, wherein at least some of the starting samples have a) a varying concentration of the target nucleic acid and/or b) varying target nucleic acids. In some embodiments, sets of droplets from different starting samples form a train of alternating droplets in the continuous flow of the carrier fluid in the channel. These and other embodiments of the invention are described in detail below.

BRIEF DESCRIPTION OF THE FIGURES

FIG. 3 shows fluorescence signals from four sets of ten droplets with decreasing template concentrations as shown in FIG. 1. The plots compare fluorescence measurements taken at cycle 7 (FIG. 3A) and 42 (FIG. 3B).

FIG. 4 shows amplification traces based on the study described in Example 2.

DETAILED DESCRIPTION OF THE INVENTION

General Methods

Figure 1:
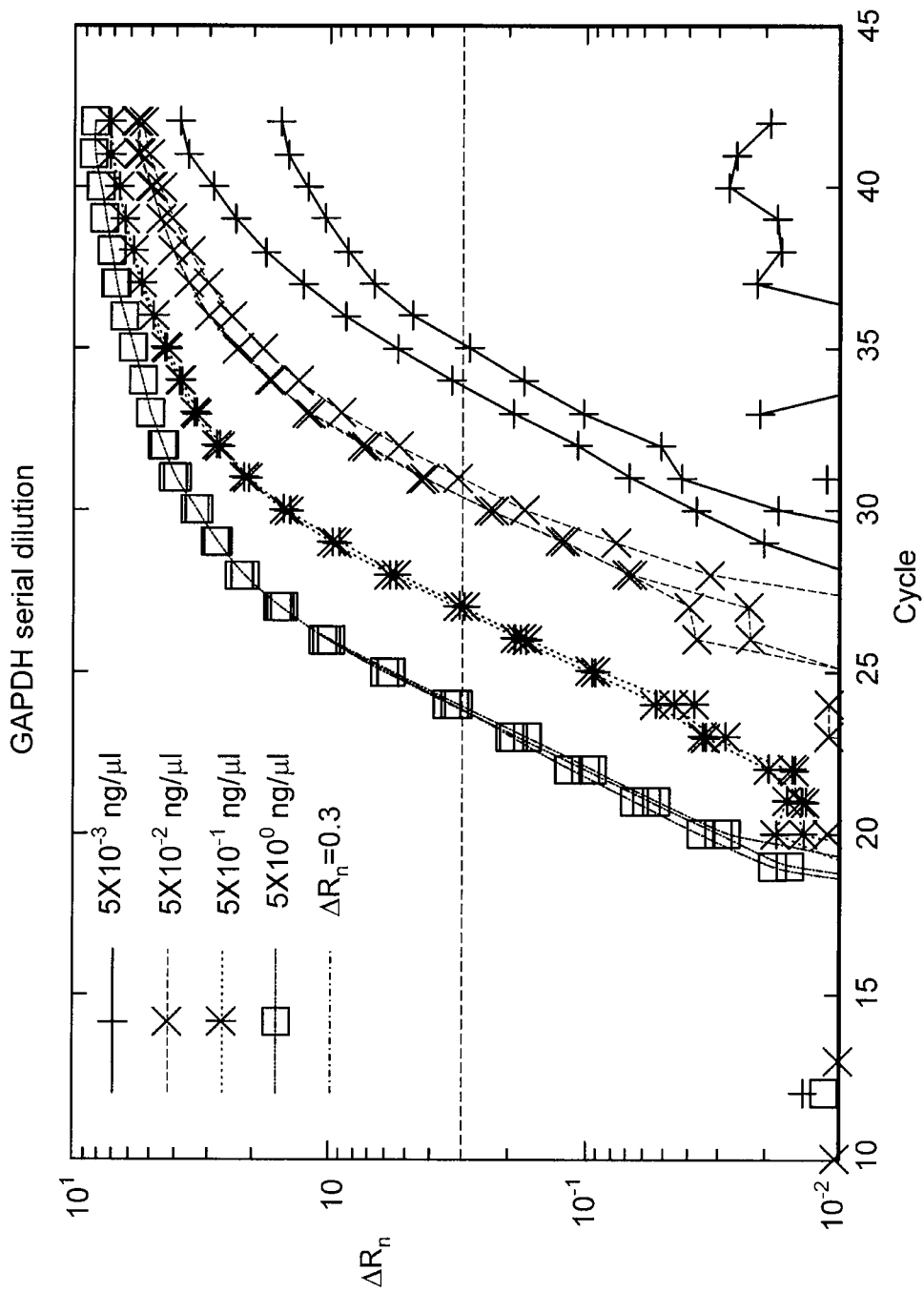
FIG. 1 illustrates amplification curves for a serially diluted sample at four concentrations of GAPDH cDNA: 5, 0.5, 0.05 and 0.005 ng/µl. The amplification was performed as described in Example 1. The intersection of each amplification curve with the threshold, as set at 0.3 here, defines the Ct value.

The invention provides methods of conducting a nucleic acid amplification reaction, such as PCR in a sample containing or suspected to contain a target nucleic acid to be detected. Although the methods described here employ the PCR as an amplification method of choice, alternative techniques of nucleic acid amplification may similarly be used in place of the PCR. Such techniques include for example, the ligase chain reaction (LCR), the transcription based amplification system (TAS), the nucleic acid sequence-based amplification (NASBA), the strand displacement amplification (SDA), rolling circle amplification (RCA), hyper-branched RCA (HRCA), etc.

In general, the invention relates to the so-called "digital PCR" and similar methods that allow one to quantify the starting copy number of a nucleic acid template, by segmenting the starting sample to smaller reaction volumes, most of which contain one copy of the target or fewer.

Methods of the invention may be used for determining the presence or the amount of a nucleic acid target, and for example, in gene expression analysis and is especially useful for lowly expressed genes.

Generally, the methods of the invention include at least the following steps:
a) providing a starting sample comprising a target nucleic acid to be detected;
b) segmenting at least part of the sample to provide a set of sample droplets in a continuous flow of immiscible carrier fluid (e.g., oil) through a channel (e.g., a capillary), each of said droplets containing on average about one copy or fewer copies of a target nucleic acid and reagents sufficient to perform a polymerase chain reaction;
c) passing the droplets through a plurality of thermal zones thereby allowing the target nucleic acid, if present, to be amplified in each droplet; and
d) detecting the presence or absence of, and/or determining the amount of, the amplified target nucleic acid in the droplets while in the flow.

In some embodiments ("real-time detection"), the step of the detecting or determining the amount is performed at multiple thermal cycles, thereby monitoring the amount of amplified target nucleic acid throughout the cycles, for example, in performing qPCR or real time PCR. Typically, the thermocycling is performed for at least a number of cycles required to reach the near-saturation level of the amplification. The number of cycles depends on the concentration of the target and other conditions and is typically between 20 and 40. The dependence of Ct on the target concentration is illustrated in Example 1. In some such embodiments, a Ct value for the target nucleic acid is determined by detecting the course of amplification at each cycle. The "real-time" detection may be used for constructing the standard curve as well as for quantifying targets in test samples.

In preferred embodiments ("end-point detection"), the step of the detecting or determining the amount is performed after the near-saturation point is reached. For the end-point detection, the starting copy number of the target nucleic acid may be determined by counting the number of positively amplified droplets in a given set of droplets.

Droplets and Samples

The starting sample contains (or is suspected to contain) at least one target nucleic acid. As used herein, the term "starting sample" refers to the sample from which droplets are generated. For example, the starting sample may be placed in a well in a conventional 384-well place, from which sample droplets are drawn. The starting sample volumes may vary, and may be, for example, 0.05-5000 µl, preferably, 5-3500 µl, e.g., 5-1000 µl, 50-500 µl, 100-350 µl. In some embodiments, droplets created by segmenting the starting sample are merged with a second set of droplets comprising one more primers for the target nucleic acid to produce final droplets. In some embodiments, the starting sample contains at least 2, 5, 10, 100, 500, 1000 or more copies of the target nucleic acid.

The sample droplets have volumes of 0.1 pl-500 nl, preferably, 1 pl-500 nl, 10 pl-500 nl, 100 pl-500 nl, 1-500 nl, or 10-500 nl, more preferably, 30-350 nl. In certain embodiments, sample droplets have volumes of 50-500, 100-500, 150-500, 200-500, 50-400, 100-400, 150-400, 200-400, 50-300, 100-300, 150-300, 200-300, or 150-250 nl. These volumes may include volumes of reagents (e.g., primer solution) added prior to the detection step. In some embodiments, the droplets are spherical, while in other embodiments, the droplets are elongated along the axis of the channel.

The number of droplets in a set being analyzed is such that their combined volume is representative of the starting sample. The set of droplets contain the entire starting sample or only its part, depending on the number of copies of the target nucleic acid present, or suspected to be present, in the starting sample. For example, a set of droplets containing, in total, 10% of the starting sample volume may be considered representative for a starting sample containing 100 copies of the target nucleic acid. Therefore, depending on the expected number of the set of analyzed droplets, the sets may contain several droplets to several thousand droplets. In some embodiments, the set of droplets for a given target nucleic acid contains, e.g., 5-10000 droplets, e.g., 100-5000, 5-1000, 100-500, 5-50, 6-30, 10-25, 8 or more, or 10 or more droplets. In other embodiments, at least 10%, 20%, 30%, 40%, 50%, 60%, 70%, 80%, or 90% of the starting sample, or the entire starting sample, is segmented into droplets.

The standard digital PCR aims at determining the dilution of the sample at which only half of segmented volumes are positive. This dilution indicates that the target nucleic acid is diluted on average to ½ per segmented volume. The present method allows one to analyze a much greater number of segmented volumes, many of which may be blank. In some embodiments, at least 30%, 40%, 50% 60%, 70%, 80%, 90%, 95%, 99% or more droplets in a set do not contain a target nucleic acid. For instance, for end-point detection, fewer than 50% (e.g., 30%, 20%, 10%, 5% or less) of droplets in the set of 10 or more (e.g., 20, 50, 100, 1000, 5000, or 10000) are positively amplified. Accordingly, in some embodiments, regardless of volume, the starting sample contains one genome equivalent of nucleic acid or less. In certain applications, it may be assumed that the mass of DNA is ~3 pg per genome (e.g., 3.3 pg/genome).

A sample may be divided into replicates (e.g., duplicates, triplicates, etc.), in which the expression levels are measured. The sample may be derived from the same source and split into replicates prior to amplification. Additionally, one may create serial dilutions of the sample. Replicate and dilution samples may be analyzed in a serial or a parallel manner. In a parallel processing system, sets of droplets corresponding to separate starting samples form a sequence of alternating droplets which pass through a thermal cycler, where droplets are being amplified, for example, as described in WO 2008/038259. A plurality of starting samples with varying concentrations of the target nucleic acid and/or varying target nucleic acids may be processed in this manner in parallel.

A sample may contain material from obtained cells or tissues, e.g., a cell or tissue lysate or extract. Extracts may contain material enriched in sub-cellular elements such as that from the Golgi complex, mitochondria, lysosomes, the endoplasmic reticulum, cell membrane, and cytoskeleton, etc. In some embodiments, the biological sample contains materials obtained from a single cell. Biological samples may come from a variety of sources. For example, biological samples may be obtained from whole organisms, organs, tissues, or cells from different stages of development, differentiation, or disease state, and from different species (human and non-human, including bacteria and virus). The samples may represent different treatment conditions (e.g., test compounds from a chemical library), tissue or cell types, or source (e.g., blood, urine, cerebrospinal fluid, seminal fluid, saliva, sputum, stool), etc. Various methods for extraction of nucleic acids from biological samples are known (see, e.g., Nucleic Acids Isolation Methods, Bowein (ed.), American Scientific Publishers (2002). Typically, genomic DNA is obtained from nuclear extracts that are subjected to mechanical shearing to generate random long fragments. For example, genomic DNA may be extracted from tissue or cells using a Qiagen DNeasy Blood & Tissue Kit following the manufacturer's protocols.

In case of the RNA analysis (e.g., mRNA, siRNA, etc.), for example, as in the case of gene expression analysis, the nucleic acid is initially reverse-transcribed into cDNA prior to conducing the PCR. This type of PCR is commonly referred to as "RT-PCR" and is illustrated in the Examples.

Droplet-in-Oil Systems

Any suitable device may be used to practice the methods of the invention. Generally, a PCR device contains a sample preparation system, a thermocycler, and a detection unit. During sample preparation, the sample is segmented into droplets which are wrapped in immiscible fluid (e.g., silicone oil, mineral oil) which continuously flows through the channel, such as a capillary having a circular cross-section. The oil, enveloping each droplet, avoids cross contamination between the sequential droplets and carry-over contamination. The sample may be pre-mixed with the primer, or the primer may be added to the droplet. In some embodiments, droplets created by segmenting the starting sample are merged with a second set of droplets comprising one or more primers for the target nucleic acid in order to produce final droplets. The merging of droplets can be accomplished using, for example, one or more liquid bridges as described in WO 2007/091230 (U.S. Ser. No. 12/093,132) and WO 2008/038259.

A queue of droplets from the preparation system may be passed through the thermal cycler. The velocity of the sample through the device is defined by the control of the velocity of the carrier fluid is controlled by an external pumping system. The sample undergoes the same thermal cycling and chemical reaction as it passes through N amplification cycles of the complete thermal device. This results in a maximum two-fold amplification after each cycle and a total amplification of I (1+E) N where I is the initial product, E is the efficiency of the reaction and N is the number of cycles. Fluorescent probes are contained in each sample droplet. The fluorescence level is detected in each droplet at each cycle, e.g., in the case of real-time PCR. This may involve the use of fluorescent probes, such as Taqman® probes, and intercollating fluorescent dyes, such as SYBR Green and LCGreen®, as described in, e.g., in U.S. Pat. Nos. 5,723,591 and 5,928,907; Gudnason et al., Nucleic Acids Res., 35(19):e127 (2007); and in the Examples.

An exemplary system for use with the method of the invention is described, for example, PCT Patent Application Pubs. WO 2007/091228 (U.S. Ser. No. 12/092,261); WO 2007/091230 (U.S. Ser. No. 12/093,132); and WO 2008/038259. One such system is made by Stokes Bio. Other exemplary systems suitable for use with the methods of the invention are described, for example, in Zhang et al. Nucleic Acids Res., 35(13):4223-4237 (2007) and include those made by Fluidigm, RainDance Technologies, Microfluidic Systems; Nanostream; and Caliper Life Sciences. For additional systems, see, e.g., Wang et al., J. Micromech. Microeng., 15:1369-1377 (2005); Jia et al., 38:2143-2149 (2005); Kim et al., Biochem. Eng. J., 29:91-97; Chen et al., Anal. Chern., 77:658-666; Chen et al., Analyst, 130:931-940 (2005); Munchow et al., Expert Rev. Mol. Diagn., 5:613-620

(2005); and Charbert et al., Anal. Chem., 78:7722-7728 (2006); and Dorfman et al., Anal. Chem, 77:3700-3704 (2005).

The following Examples provide illustrative embodiments of the invention and do not in any way limit the invention.

EXAMPLES

Example 1

Measurement of qPCR Amplification Efficiency by Serial Dilution

Figure 2:
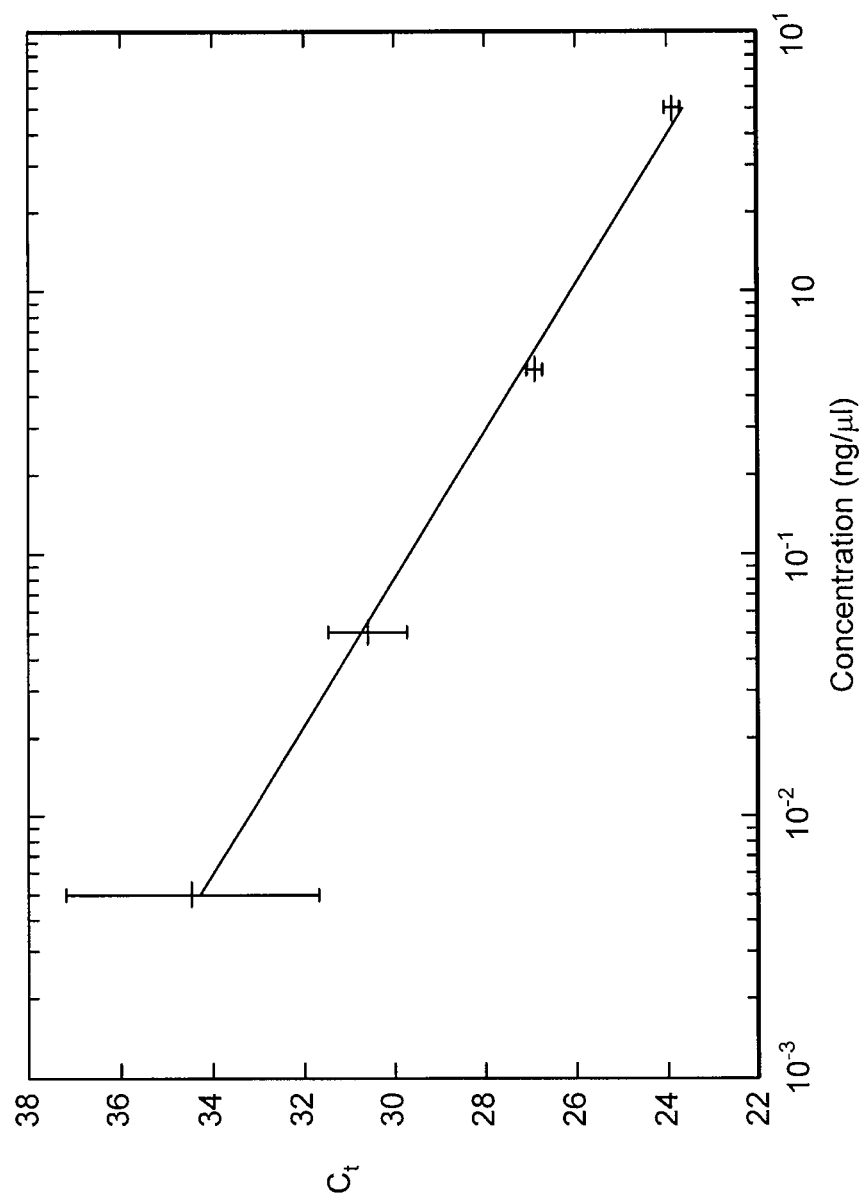
FIG. 2 shows Ct value as a function of concentrations based on the results shown in FIG. 1. The slope of the line allows the amplification efficiency to be measured.

Total RNA is extracted from cultured cells, reverse transcribed into cDNA and used as the template for the qPCR reaction. The starting concentration of the template is 5 ng/µl which is then diluted 10-fold to 0.5 ng/µl. This 10-fold dilution is repeated yielding samples with four concentrations of cDNA template: 5 ng/µl, 0.5 ng/µl, 0.05 ng/µl, and 0.005 ng/µl. The resulting amplification curves, obtained using a Stokes Bio device (www.stokesbio.ie), are shown in FIG. 1. As seen from the figure, for lower starting template concentrations, more cycles of PCR are necessary to bring the fluorescence signal to the threshold level. In fact, if the PCR reaction was 100% efficient a 0.5 ng/µl sample would require 3.32 more cycles of PCR to reach the same threshold as a 5 ng/µl sample (10 times the 0.5 ng/µl sample). The fractional cycle at which the amplification curve reaches the threshold is called the Ct value: a measure of the gene expression of the sample. The threshold is set at 0.3 read off of the corresponding Ct values for each set of amplification curves in FIG. 1. The Ct value is plotted against the cDNA concentration in FIG. 2. Analysis of this data implies that the slope of the best fit line is −3.53±0.13, estimating the amplification efficiency to be 92%±4%, which is within the range expected of qPCR on a standard PCR system, such as Applied Biosystems' 7900HT.

FIG. 3A shows the fluorescence signal from cycle 7 of a 50 cycle amplification using the Stokes Bio device. Each of the small spikes represents a droplet passing. The far left spike represents the lead droplet. The concentrations of each set of droplets range from 0.005 to 5 ng/µl, as indicated in the figure. Two aspects of the data are clearly shown—there is background fluorescence from the oil filled capillary, and background signal from each droplet—both are constant. FIG. 3B shows the same droplets at cycle 42 when amplification is complete. Note that the signal from each droplet in a set of ten varies from droplet-to-droplet. This is because the optical system for each channel is not identical. This effect is easily normalized out during data processing. At the highest level of dilution (0.005 ng/µL), only four out of ten droplets have amplified. This is a statistical effect, expected for this level of template dilution and droplet volume. The data processing algorithm is designed to take this into account.

Example 2

High Throughput qPCR Performance Validation

The analysis of gene expression is an essential element of functional genomics, and qPCR-based expression profiling is the gold standard for the precise monitoring of selected genes. Gene expression relies upon the reverse transcription of mRNA to cDNA. It is, however, generally not possible to use cDNA as a standard for absolute quantification of mRNA because there is no control for the efficiency of the reverse transcription step. This Example presents Stokes Bio's amplification representative performance data from genomic DNA (gDNA), a commonly used in standard qPCR.

Figure 4A:
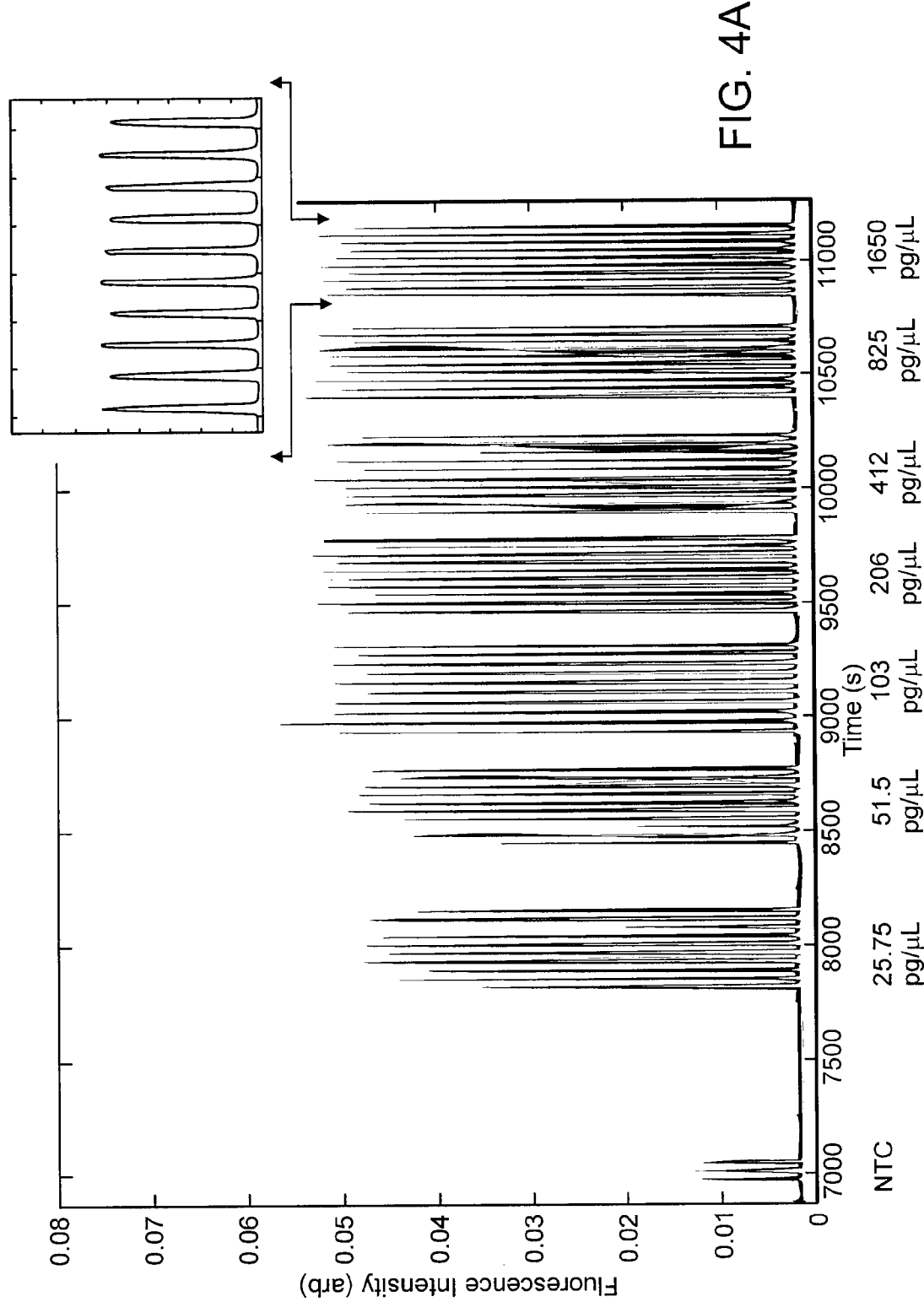
FIG. 4A shows droplet fluorescence traces of No Template Control (NTC) droplets followed by seven increasing sample concentrations at cycle 42.
Figure 4B:
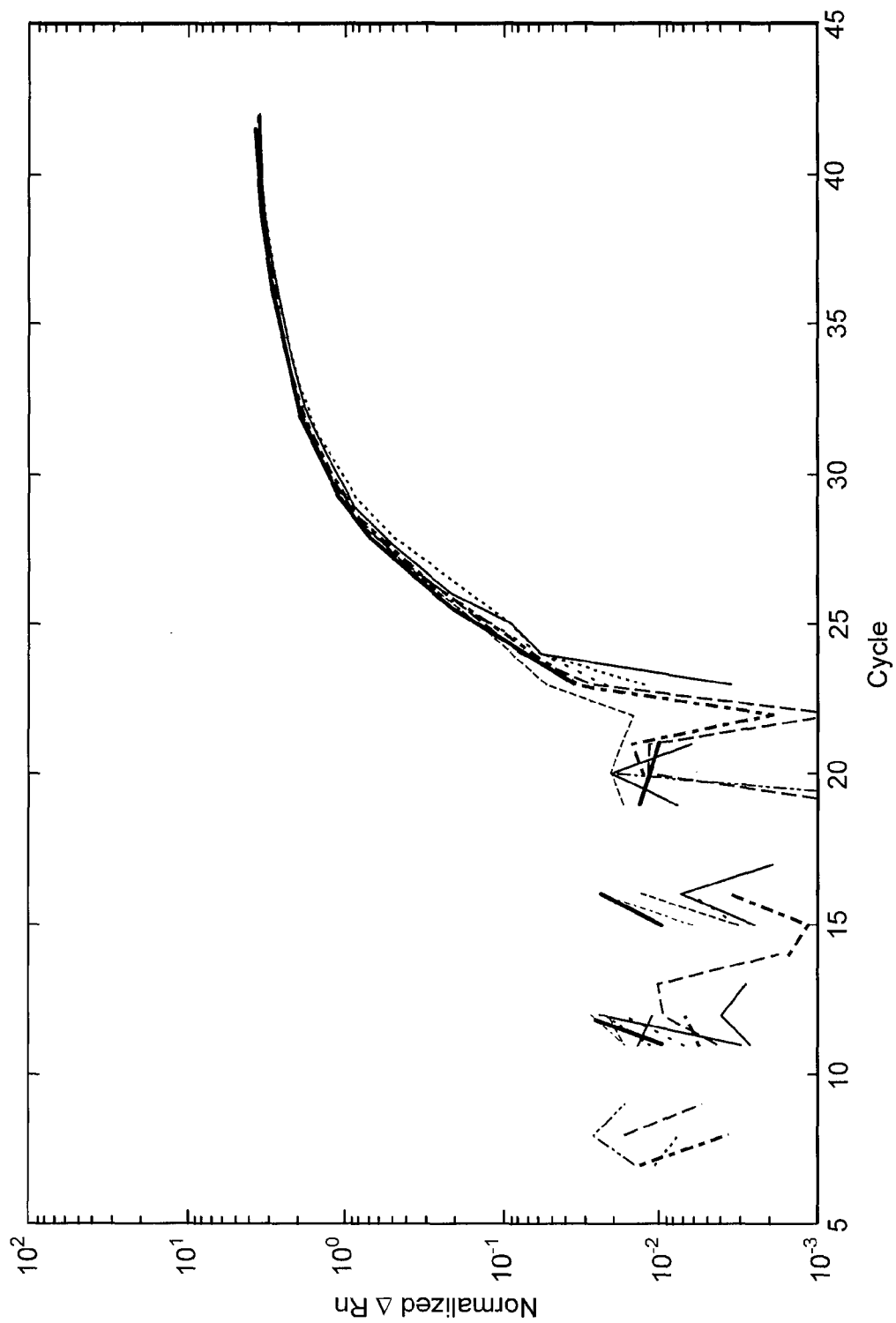
FIG. 4B shows an amplification curve of ten 1650 pg/µl droplets.
Figure 4C:
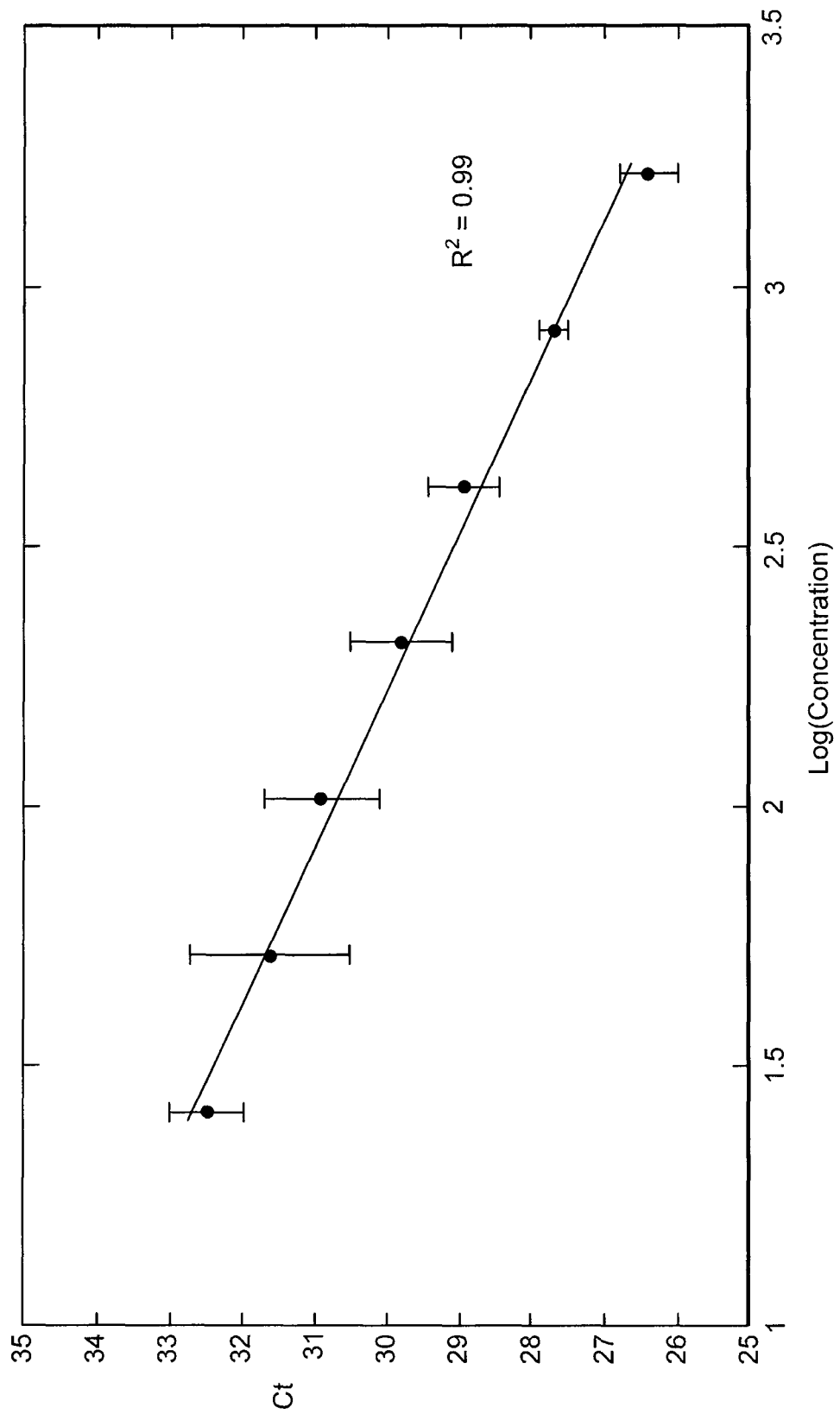
FIG. 4C illustrates the standard curve generated from Ct data showing near single molecule detection in 300 nl droplets.

A TaqMan® RNase P gene primer and probe set is used to evaluate instrument performance. The RNase P gene is a single-copy gene encoding the RNA moiety for the RNase P enzyme. Several two-fold dilutions are created from a stock of a known gDNA copy number. These dilutions were used to prepare complete qPCR reactions for amplification in the Stokes Bio instrument. Table 1 shows gDNA template concentrations with corresponding mean Cts and estimated starting copy numbers for each of the seven reaction sets. A no template control (NTC) is also included and showed no amplification. FIG. 4A shows droplet fluorescence traces of three NTC reactions with seven sets of ten 300 nl droplets. Each 10× replicate set was taken from a different concentration sample. The inset plot shows excellent data resolution for each 300 nl droplet. FIG. 4B shows a normalized amplification plot of the most concentrated reaction set with a Ct of 26.4. FIG. 4C shows a standard curve taken from the Ct data in Table 1. Error bars indicate the Ct range in each of the 10× replicate sets. Ct variability is attributable to Poisson noise or a variation in the number of starting copies from one droplet to another at a given concentration.

TABLE 1

| gDNA in pg/µl | Mean Ct | Standard Deviation | Copies* per 300 nl Reaction |
|---|---|---|---|
| 1650 | 26.4 | 0.11 | 150 |
| 825 | 27.7 | 0.16 | 75 |
| 412 | 28.9 | 0.35 | 37.5 |
| 206 | 29.8 | 0.44 | 18.75 |
| 103 | 30.9 | 3.4 | 9.4 |
| 51.5 | 31.6 | 0.76 | 4.7 |
| 25.75 | 32.47 | 0.76 | 2.34 |

*Determined using 1 copy per 3.3 pg

Example 3

Digital PCR End-Point Detection

The premise for this technique is to divide a large volume into a discreet number of smaller volumes reducing the number of copies in each sample, following the amplification process to perform fluorescence detection on the emerging droplets. The resulting total number of droplets with amplification can then be used to determine starting copy number. It also can be used for rare target detection wherein the statistic probability of amplification is increased for the rare target as the number of background molecules is reduced by the division.

Using a statistical prediction model the probability of the distributed target molecules in the segment droplets can be generated. This is particularly of benefit for low concentration samples as it provides a prediction of the number of droplets containing molecules and thus the number of droplets expected to fluoresce.

The binomial distribution model employed is a discrete probability distribution that arises in many common situations. The recognized example of binomial distribution is counting the number of heads in a fixed number of independent coin tosses, while in this case, it is counting the number of copies in a fixed known number of droplets created from the original sample. In a series of n independent trials, or n independent copies, each trial or copy results in a success (the outcome that is counted) or failure. In other words, each copy has two possible outcomes, it enters the monitored droplet or not. For a sample segmented into 3000 droplets, each copy has the same probability, p, of success, 1 in 3000, for each monitored droplet. The binomial distribution model counts the number of successes in a fixed number of trials. Binomial distribution is completely determined by two parameters; n, the number of cDNA copies in the main volume, and p, the success probability common to each copy. As a consequence, knowing the number of copies and the number of droplets allows a binomial distribution to be used.

Figure 5:
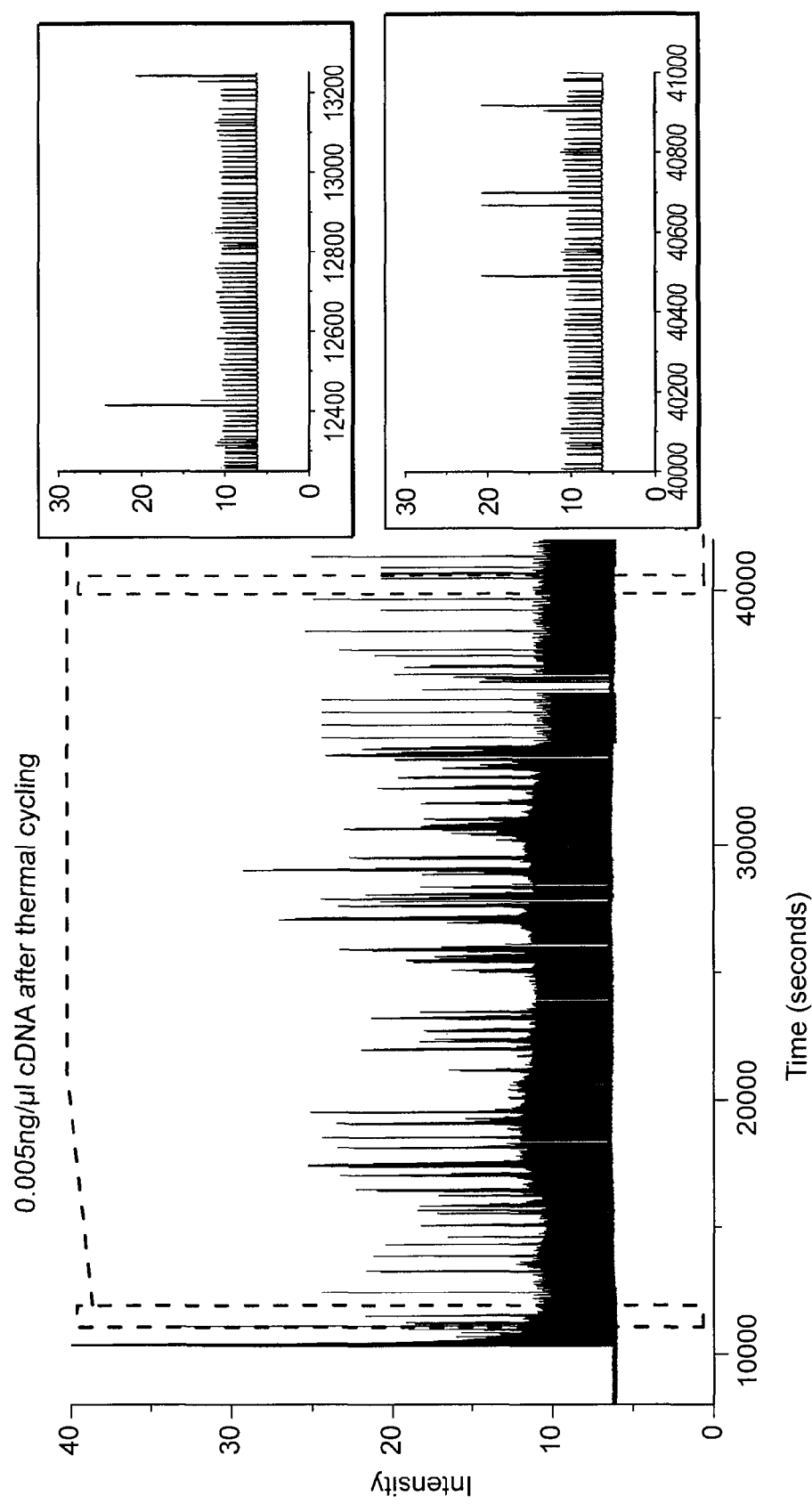
FIG. 5 demonstrates a typical PCR thermal cycling trace for a set of 3,000 droplets from a 300 µl sample having 0.005 ng/µl cDNA, performed as described in Example 3.

FIG. 5 demonstrates a typical trace for a 0.005 ng/µl sample. The data demonstrated here uses a 300 µl sample volume which is divided into ~3000 droplets of 100 nl droplet volumes.

In another experiment, digital PCR involves amplifying a single DNA template from minimally diluted samples, generating amplicons that are exclusively derived from one template. It transforms an exponential, analog signal obtained from conventional PCR to linear, digital signals, thus allowing statistical analysis of the PCR product.

To determine the mass of genomic DNA which corresponds to copy numbers of target nucleic acid sequences, the following formula was used:

$$N = (m \times N_A)/M$$
$$M = n \times 1.096 \times 10^{-21} \text{ g/bp}$$

where n is the number of base pairs, m is the mass of DNA, $N_A$ is Avogadro's number ($6.02 \times 10^{23}$ bp/mol) and M is the average molecular weight of a base pair.

A series of 2-fold dilutions of human genomic DNA 10 ng/µl was carried out. The gene of interest was the RNAse P gene which exists as a single copy per haploid genome. Based on the above formulae, the copy numbers of the RNAse P gene per 350 nl droplet are shown in Table 2.

TABLE 2

| Copy No | gDNA Mass (pg) | Rxn Vol. | Conc. pg/µL | RNAse P Copies 20 µl | Copies/ 350 nl |
|---|---|---|---|---|---|
| 10000 | 33000 | 5 | 6600 | 10000 | 175.00 |
| 5000 | 16500 | 5 | 3300 | 5000 | 87.50 |
| 2500 | 8250 | 5 | 1650 | 2500 | 43.75 |
| 1250 | 4125 | 5 | 825 | 1250 | 21.88 |
| 625 | 2062.5 | 5 | 413 | 625 | 10.94 |
| 312.5 | 1031.25 | 5 | 206 | 312.5 | 5.47 |
| 156.25 | 515.625 | 5 | 103 | 156.25 | 2.73 |
| 78.125 | 257.8125 | 5 | 52 | 78.125 | 1.37 |
| 39.0625 | 128.90625 | 5 | 26 | 39.0625 | 0.68 |

Mass DNA/genome was assumed to be 3.3 pg/genome. PCR amplification was carried out on the Stokes HTI on a series of 10 No Template Controls (NTCs) followed by 10 droplets of 350 nl volume at each copy number. Results indicate that at low copy numbers, discrete amplification of droplets occurred. S-curve analysis of this amplification seemed to indicate that threshold cycle (Ct) values clustered around distinct Ct values.

All publications, patents, patent applications, and biological sequences cited in this disclosure are incorporated by reference in their entirety.

What is claimed is:

1. A method of conducting a nucleic acid amplification reaction, the method comprising:
   providing at least one starting sample comprising at least one nucleic acid;
   segmenting at least part of the at least one starting sample to provide a set of sample droplets in a continuous flow of immiscible carrier fluid through a channel, each of said droplets of the set of sample droplets containing on average about one or fewer copies of a target nucleic acid;
   merging the set of sample droplets with a second set of droplets having one or more primers to form a set of combined droplets;
   passing the set of combined droplets through a plurality of thermal zones thereby allowing the target nucleic acid, if present, to be amplified in each droplet;
   determining a Ct value of the target nucleic acid for at least one of the combined droplets;
   detecting the presence or absence of, and/or determining the amount of, the amplified target nucleic acid in the droplets within the set of combined droplets while in the flow by analyzing the Ct value based on real-time amplification data;
   determining the total number of combined droplets with amplified target nucleic acid; and
   determining the starting copy number based on determining the total number of combined droplets with amplified target nucleic acid.

2. The method of claim 1, wherein the volume of each droplet of the set of combined droplets is 0.1 pl-500 nl.

3. The method of claim 2, wherein the volume of each droplet of the set of combined droplets is 10-500 nl.

4. The method of claim 3, wherein the volume of each droplet of the set of combined droplets is 30-350 nl.

5. The method of claim 1, wherein a portion of the sample representative of the entire sample is segmented into the droplets.

6. The method of claim 5, wherein the starting sample contains at least 10 copies of the target nucleic acid and at least 10% of the sample is segmented.

7. The method of claim 5, wherein the set of sample droplets contains 5-50 droplets.

8. The method of claim 5, wherein the set of sample droplets from the starting sample contains 100 or fewer droplets, each of 500 nl or less.

9. The method of claim 1, wherein at least 50% of droplets in the set of sample droplets do not contain the target-nucleic acid.

10. The method of claim 1, wherein detecting the presence or absence of, and/or determining the amount of, the amplified target nucleic acid in the droplets is performed at multiple thermal cycles, thereby monitoring the amount of amplified target nucleic acid throughout the cycles.

11. The method of claim 1, wherein fewer than 50% of droplets in the set of combined droplets are positively amplified.

12. The method of claim 1, wherein the method comprises reverse transcription of mRNA to prepare the starting sample.

13. A method of processing a plurality of starting samples in parallel, each according to claim 1, wherein at least some of the starting samples have (a) varying concentration of the target nucleic acid and/or (b) varying target nucleic acids.

14. The method of claim 13, wherein the parallel processing comprises sets of combined droplets from different samples that form a train of alternating combined droplets in the continuous flow in the channel.

15. The method of claim 1, wherein the droplets of the set of combined droplets remain wrapped in the immiscible carrier fluid while in the flow.

16. The method of claim 1, wherein the channel comprises a capillary having a circular cross-section.

17. The method of claim 1, wherein the droplets of the set of sample droplets are spherical.

18. A method of conducting a nucleic acid amplification reaction, the method comprising:
   providing a starting sample containing approximately at least one nucleic acid;
   segmenting at least part of the sample to provide a set of at least 10 sample droplets in a continuous flow of immiscible carrier fluid through a channel, each of said droplets of the set of sample droplets containing on average about one or fewer copies of a target nucleic acid;
   merging the set of sample droplets with a second set of droplets having one or more primers to form a set of combined droplets;
   passing the set of combined droplets through a plurality of thermal zones thereby allowing a target nucleic acid, if present in the combined droplets, to be amplified to near or above saturation level; and
   determining a Ct value of the target nucleic acid for at least one of the combined droplets
   detecting the presence or absence of, and/or determining the amount of, the amplified target nucleic acid in the combined droplets while in the flow by analyzing the Ct value based on real-time amplification data;
   determining the total number of combined droplets with amplified target nucleic acid; and
   determining the starting copy number based on determining the total number of combined droplets with amplified target nucleic acid.

19. The method of claim 1 further comprising flowing more than one sample.

20. The method of claim 1, wherein the segmenting includes segmenting the sample into 1 pL-10 pL droplets.

21. The method of claim 1, wherein the merging includes using a passive system to merge the droplets.

22. The method of claim 1, further comprising determining the mass of the target nucleic acid.

23. The method of claim 22, wherein the target nucleic acid is DNA.

24. The method of claim 23, wherein the DNA is genomic DNA.

25. The method of claim 24, wherein the mass of genomic DNA corresponds to copy numbers of target nucleic acid sequences.

* * * * *